(12) United States Patent
Horch

(10) Patent No.: US 7,047,152 B2
(45) Date of Patent: May 16, 2006

(54) METHOD AND A SYSTEM FOR EVALUATION OF STATIC FRICTION

(75) Inventor: Alexander Horch, Heidelberg (DE)

(73) Assignee: ABB AB, Västerås (SE)

( * ) Notice: Subject to any disclaimer, the term of this patent is extended or adjusted under 35 U.S.C. 154(b) by 0 days.

(21) Appl. No.: 10/436,444

(22) Filed: May 13, 2003

(65) Prior Publication Data

US 2004/0078168 A1    Apr. 22, 2004

Related U.S. Application Data

(63) Continuation of application No. PCT/SE01/02460, filed on Nov. 8, 2001.

(51) Int. Cl.
*G01C 9/00* (2006.01)

(52) U.S. Cl. .................. 702/154; 702/181; 702/183; 73/9; 73/865.9

(58) Field of Classification Search ............. 702/154, 702/181, 183, 33; 73/9, 865.9, 19; 310/328, 310/323.01, 325
See application file for complete search history.

(56) References Cited

U.S. PATENT DOCUMENTS

| | | | | |
|---|---|---|---|---|
| 4,939,922 A | * | 7/1990 | Smalley et al. | 73/10 |
| 5,542,281 A | * | 8/1996 | Lee et al. | 73/9 |
| 5,750,879 A | * | 5/1998 | Ohtsuka et al. | 73/9 |
| 6,664,714 B1 | * | 12/2003 | Magnussen et al. | 310/354 |
| 6,690,101 B1 | * | 2/2004 | Magnussen et al. | 310/328 |

OTHER PUBLICATIONS

M. Ruel, P.E., Loop Optimization: Troubleshooting, Diagnose Loop Behavior to Find and Correct Problems with Final Control Elements, the Environment, and Upstream Systems Before You Tune the Controller, Control Magazine, Apr. 1999, 7 pages.

A. Horch, A Simple Method for Detection of Stiction in Control Valves, Control Engineering Practice 7, 1999, pp. 1221-1231.

T. Miao et al., Automatic Detection of Excessively Oscillatory Feedback Control Loops, Proceedings of the 1999 IEEE, International Conference on Control Application Kohala Coast Island of Hawaii, Aug. 22-27, 1999, pp. 359-364.

R. Deibert, Model Based Fault Detection of Valves in Flow Control Loops, IFAC Fault Detection, Supervision and Safety for Technical Processes, Espoo, Finland, 1994, pp. 417-422.

(Continued)

*Primary Examiner*—John Barlow
*Assistant Examiner*—Hien Vo
(74) *Attorney, Agent, or Firm*—Venable LLP; Eric J. Franklin

(57) ABSTRACT

A method for evaluation whether oscillations in a control process depend on static friction in an actuator. A signal from the actuator or the signal from the process is measured. The measured signal is signal processed for the purpose of detecting whether the measured signal comprises abrupt inclination changes. It is decided whether there is static friction in the actuator based on whether the signal comprises abrupt inclination changes.

16 Claims, 2 Drawing Sheets

OTHER PUBLICATIONS

O. Taha et al., Detection and Diagnosis of Oscillations in Control Loops, Proceedings of the 35th Conference on Decision and Control, Kobe, Japan, Dec. 1996, pp. 2432-2437.

A. Wallén, Valve Diagnostics and Automatic Tuning, Proceedings of the American Control Conference, Albuquerque, New Mexico, Jun. 1997, pp. 2930-2934, T. Hägglund, A Control-Loop Performance Monitor, Control Eng. Practice, vol. 3, No. 11, pp. 1543-1551, 1995.

K. Forsman et al., A New Criterion for Detecting Oscillations in Control Loops, European Control Conference, Karlsruhe, Germany, 1999, CP8-3, 4 pages.

A. Horch et al., A Method for Detection of Stiction in Control Valves, IFAC On-Line Fault Detection and Supervision in the Chemical Process Industries, Lyon, France, 1998 pp. 257-262.

Lin et al., Several Practical Issues in Control Loop Monitoring and Diagnosis, R. Ritala, Control Systems '98 Information Tools to Match the Evolving Operator Role, pp. 245-250.

* cited by examiner

US 7,047,152 B2

METHOD AND A SYSTEM FOR EVALUATION OF STATIC FRICTION

This application is a continuation of PCT/SE/01/02460 filed 8 Nov. 2001.

FIELD OF THE INVENTION

The present invention relates to a method and a system for evaluation of whether oscillations in a control process depend on static friction in an actuator.

The invention also relates to a computer program product, which when it is run on a computer, performs a method for evaluation whether oscillations in the control process depend on static friction in the actuator, and a computer readable medium comprising the computer program product.

Control processes are common in the industry, for instance in the pulp and paper and oil industry. Undesired oscillations in the control signals have a negative effect on the performance and may, for example, depend on poor adjustment of the control system, the occurrence of disturbances in the process or high static friction in the actuator. Valves are a kind of actuator, in which problems with high static friction often occurs.

PRIOR ART

Friction exists between two bodies being in contact with each other. When the bodies are resting in relation to each other, there is static friction between them and when they are moving relative to each other, there is kinetic friction between them. Acquired by experience, the kinetic friction is less than the static friction.

Friction occurs in actuators for control processes. In particular, in actuators in which both movement between the contact bodies and resting occur, such as for valves. When the actuators become old and worn, which may appear as loose, corrosion, cavitations on contact surfaces, dirt particles in the lubricant, etc., the static friction will increase. When the friction increases, the difference between friction in rest and movement becomes larger.

This relation between the frictions causes a jerky movement of the valve member with abrupt changes of the position, resulting in abrupt changes of the process. This jerky movement ("stick-slip") of the valve member depends of the alternation between rest and relative movement of members comprised in the actuator, and thus the change between static and kinetic friction. This problem appears at slow regulation of the position of the actuator and in particular at start and stop. For instance, when a resting actuator shall be fine adjusted, it receives a control signal adjusting the force, which is about to bring the actuator to the desired position. This force, which affects the actuator, has to overcome the static friction to achieve the adjustment. When the force is larger than the static friction, the actuator begins to move, and in that moment the friction changes from static to kinetic. The applied force usually becomes too large when the actuator begins to move, especially at small adjustments of the position of the actuator, which results in an over-steering. When the control system is about to compensate for the over-steering, the same procedure is repeated, but in the opposite direction. Due to this interaction, the whole control system may become unstable, followed by very heavy oscillations.

To be able to do something about the problem with oscillations when they occur in a control system, it is desirable to receive knowledge about whether the reason for the oscillations is static friction in the actuator.

It is well known to indicate the existence of static friction in actuators using a method based on the cross-correlation between the output signal of the process and the control signal of the actuator. This is shown in an article "A simple method for detection of striction in control valves" written by A. Horsch. Cont. Eng. Pract., 7(10):1221–1231, October 1999. Such a cross-correlation is a statistic notion stating how time series vary in correlation. If the oscillations in a control process depend on static friction, the cross-correlation will be an odd function with regard to the origin, and if there is essentially no static friction, the cross-correlation will be an even function with regard to the origin. By using this fact, it is possible for certain control processes to decide whether the oscillations depend on static friction or not.

The disadvantage with such a method is that it is not applicable for integrating control processes. The reason why the known method cannot handle to the evaluation of the reason for oscillations in integrated control processes is that the cross-correlation in those processes can be an odd function even for oscillations that do not depend on static friction. Accordingly, using the cross-correlation gives no directions about the reason for the oscillations and even less directions on whether it is static friction that causes the problem.

SUMMARY OF THE INVENTION

The object of the present invention is to provide a method for evaluation whether oscillations in a control process depend on static friction in an actuator, which method serves this purpose for both integrating processes and for non-integrating processes, so-called self-regulating processes, and which method further is simple and robust.

This object is achieved by a method comprising the step of measuring the signal from the actuator or the signal from the process, signal processing the measured signal for the purpose of detecting whether the measured signal comprises abrupt inclination changes, and deciding whether there is static friction in the actuator based on whether the signal comprises abrupt inclination changes. The method according to the invention uses the fact that if the signal oscillates due to static friction in the actuator, the signal from the actuator and from the process show frequent fast inclination changes, but if the signal oscillates for any other reasons, the signal shows continuous soft inclination changes. A signal oscillating due to static friction is often triangular, while a signal oscillating for other reasons is mainly sinusoidal. By detecting whether the signal comprises abrupt inclination changes, it is possible to decide whether the signal is oscillating due to static friction.

In an embodiment of the invention, the measured signal is derived at least once, and based on the derived signal it is determined whether there is static friction in the actuator. An easy way to determine whether the signal comprises abrupt inclination changes is to study the derivative of the signal. Abrupt inclination changes can be detected by detecting whether the derivative of the measured signal comprises abrupt changes. Depending on whether the derivative of the signal comprises abrupt changes, it is decided whether there is static friction in the actuator.

In an embodiment of the invention, a first mapping of the derived signal is calculated and compared with a second mapping representing an output signal at static friction, and a third mapping representing an output signal without static friction, and based on the comparison it is decided whether there exists static friction In the actuator. Preferably, the third mapping represents an output signal oscillating mainly sinusoidal. By calculating a suitable mapping of the derived signal and then comparing it with a theoretically calculated mapping of a typical output signal at static friction and a typical output signal when there is no static friction it is possible to achieve an automatic method for evaluation of whether the signal oscillates due to static friction.

In a further embodiment of the invention, the second derivative of the signal from the process or the first derivative of the signal from the actuator is calculated if the control process is an integrated process. If the control process instead is a self-regulating process, the first derivative of the signal from the process or the first derivative of the signal from the actuator is calculated. By choosing between deriving once or twice, the method according to the invention may be applied on both a self-regulating process and an integrated process. Accordingly, there are two possibilities to choose between, measuring the signal from the process or measuring the signal from the actuator. The signal from the actuator is often difficult to reach for measuring, and thereby the signal is not always available. If the signal from the actuator is available, it is better to use it, since it comprises fewer disturbances than the signal from the process.

According to a further embodiment of the invention, the frequency of the measured signal is calculated and the measured signal is filtered in a filter having a filter bandwidth in the interval 2–4 times the measured frequency. When a signal is derived, the noise is also derived. For achieving as good an evaluation as possible, the signal is filtered. For the filtering, the choice of filter bandwidth is important since it is desirable to keep as much information as possible in the signal, while the disturbing noise is removed. It has been shown that a filter bandwidth in the interval 2–4 times the frequency of the signal, and preferably within the interval 2,5–3,5 times the frequency of the signal is suitable for this purpose.

In a preferred embodiment of the invention, a probability distribution is calculated for the derived signal and in accordance with the calculated distribution it is determined whether there is static friction in the actuator. In this embodiment, the mapping of the derived signal is a calculated probability distribution. By using a probability distribution for determining whether there exists static friction in the actuator, a simple and robust method possible to carry out in an automatic way is obtained.

According to an embodiment of the invention, the calculated probability distribution is compared to a second and a third probability distribution, wherein the second probability distribution represents an output signal at static friction and the third probability distribution represents an output signal oscillating for any other reason, and based on the comparison, it is determined whether there is static friction in the actuator. The second and the third probability distribution differ in that the second probability distribution has one maximum and the third probability distribution has two maxima. Accordingly, a simple comparison between the probability distributions can determine whether the oscillations depend on static friction or not.

In an embodiment of the invention, an adaption of the second and the third probability distribution to the calculated probability distribution for the derived signal is performed before the comparison. For an easy and correct determination of which one of the probability distributions is most similar to the probability distribution of the derived signal, the second and the third probability distributions are adapted to the probability distribution of the derived signal.

In an embodiment of the invention, the second probability distribution represents an output signal mainly comprising white noise, and the probability distribution has an essentially gaussian shape. Such a distribution is simple to adapt to the probability distribution for the derived signal and is a sufficient representation of a probability distribution for a signal oscillating due to static friction. The third probability distribution represents an output signal comprising a sinus signal and white noise. Such a distribution is also easy to adapt to the probability distribution for the derived signal and is a sufficiently representation of a probability distribution for a signal oscillating for other reasons than static friction.

In an embodiment of the invention, said adaption is achieved by, for each of the second and the third probability distribution, estimating the standard deviation which provides the best adaption to the probability distribution for the derived signal. By varying the standard deviation, the adaption of the probability distributions may be simply achieved.

According to a further embodiment of the invention, the amplitude for the oscillations in the measured signals is estimated and the standard deviation for the third probability distribution shall be less than 40% of the amplitude. In the case when the signal oscillates due to static friction, the adaption of the third signal should not be driven so far that it becomes transferred to a gaussian curve having only one maximum. To prevent this, a restriction is introduced stating that the standard deviation is not allowed to exceed 40% of the amplitude.

According to a further embodiment of the invention, said comparison is performed by calculating a first value corresponding to the difference between the first and the second probability distribution, and a second value corresponding to the difference between the first and the third probability distribution, and comparing the first and the second values with each other, and if the values differ with more than 10% and the first value is less than the second value, there is static friction. By calculating the values corresponding to the difference between the probability distributions and comparing them with each other, it is possible to decide whether the signal is oscillating due to static friction or not and further, a measure of the certainty of the evaluation is obtained. If the signals differ less than 10%, the uncertainty of the evaluation is so high that it is best not to make any statement.

A further object of the invention is to provide a system for evaluation whether oscillations in a control process depend on static friction in an actuator. The object is achieved by a system characterized in that it comprises a measuring device for measuring the signal from the actuator or the signal from the process, and a signal processing means, which decides whether the measured signal comprises abrupt inclination changes. The term, measuring device, relates to an analogue or digital measuring device for measuring any process variables, for example temperature, pressure, and flow. In a preferred embodiment, in which the actuator is a valve, the invention may be used advantageously in connection with a measuring signal from a measuring device measuring the level in a liquid. The signal processing means may, for example, comprise a processor and memories.

According to an embodiment of the invention, the signal processing means comprises a derivation means for determining the first and the second derivative of the measured signal, and a calculation member which, based on the derivative of the measured signal, calculates one or several values which depend on whether there is static friction in the actuator.

The invention also relates to a computer program product and a computer readable medium according to the corresponding appended claims. It is easily realized that the method as defined in the appended set of method claims is well suited for being executed by a processor according to a computer program comprising instructions for performing the steps in the method. Although, it is not explicitly expressed in the claims, the invention includes such program products that may be combined with a method according to any of the appended method claims.

BRIEF DESCRIPTION OF THE DRAWINGS

The present invention will now be explained more closely by the description of different embodiments and with reference to the appended drawings.

FIGS. 2a–2c show a first type of output signals from an integrated control process oscillating due to static friction, wherein FIG. 2a shows the fundamental form of the output signal, FIG. 2b shows its first derivative, and FIG. 2c its second derivative.

FIGS. 3a–3c show a second type of output signals from an integrated control process oscillating for another reason than static friction, wherein FIG. 3a shows the fundamental form of the output signal, FIG. 3b shows its first derivative, and FIG. 3c shows its second derivative.

DESCRIPTION OF EMBODIMENTS

The invention is particularly suitable for diagnosing of static friction in actuators. In particular, the invention is useful for actuators comprising valves and will be explained in connection with such actuators. The method according to the invention is suitable in areas comprising all types of actuators with liner as well as non-liner mobility.

The method according to the invention uses the fact that regular, abrupt changes of the position of the valve cause abrupt inclination changes in the output signal of the control system. This occurs, for example, when the valve is old, and it responses with a jerky movement to a control signal ordering a change in the position, due to the static friction increased by the time. When the output signal of the control system oscillates for another reason, the output signal is supposed to oscillate essentially sinusoidally.

For the method according to the invention to be applicable, it is necessary to first find out if the output signal from the control process is oscillating. This may be detected by some known method, for example, according to the publication "A New Criterium for Detecting Oscillations in Control Loops" written by K. Forsman and A Stattin. European Control Conference, Karlsruhe, Germany, 1999, CP8-3. In the following, it is assumed that it has already been determined that the output signal from the control process is oscillating.

Figure 1:
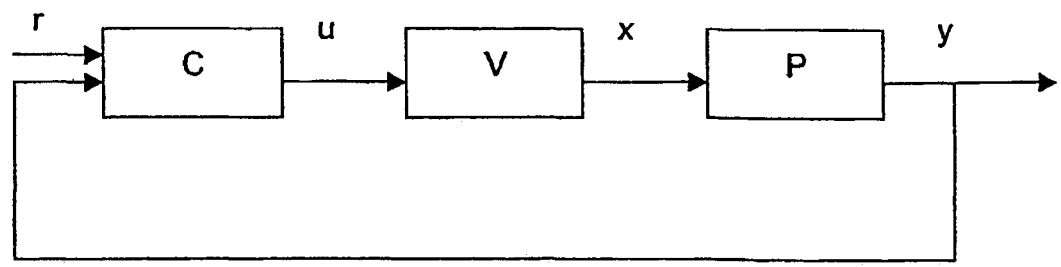
FIG. 1 shows schematically a block-diagram of a control circuit.

FIG. 1 shows a block scheme of a control process comprising a regulator unit C, a valve V, a process P. In the figure, the set point of the regulator is denoted r, the output signal from the process is denoted y, the output signal from the valve is denoted x, and the output signal from the regulator unit is denoted w.

According to the method according to the invention, it is particularly advantageous to regard the output signal when it is derived, since the difference in shape between a signal having abrupt inclination changes and a signal with a sinusoidal characteristic then clearly appears. Such a distinctive difference appears when the output signal in question is differentiated to certain extent. This extent is achieved for a self-regulating control process when its output signal is derived once and for an integrating control process when its output signal y is derived twice. If the output signal x from the actuator is available, it is possible to use it, whereby its first derivative shows the desired distinctive signal characteristic. Thanks to these distinctive differences, which are obtained when the output signal is derived, possibilities are created for an automatic method for detecting the presence of static friction. A processor in a computer controlled by a computer program may advantageously carry out this method. Such a computer program may advantageously be provided by a distribution system and/or over a network, such as Internet.

Even though the method according to the invention is suitable for any regulation processes for a non-limit purpose in the following the method will be described for an integrating control process.

For evaluation of whether oscillations in a control process depend on static friction in the valve, in this embodiment the output signal y from the process is measured. For the purpose of avoiding that the noise from the measured output signal decreases the accuracy, the signal is filtered, so that high disturbing frequencies are removed. If the oscillating frequency of the output signal is known, may a suitable filter bandwidth, such as a limit, cut the exceeding frequencies. The frequency of the oscillation can easily be determined by any known method. A suitable filter bandwidth should lay within an interval 2–4 times the measured frequency, preferably within 2,4–2,5 times the measured frequency. After filtering, the measured signal is derived at least once, and based on this signal it Is determined whether there is static friction in the actuator. If the signal is derived twice, the signal is filtered a second time between the derivations.

Figures 2A, 2B, 2C:
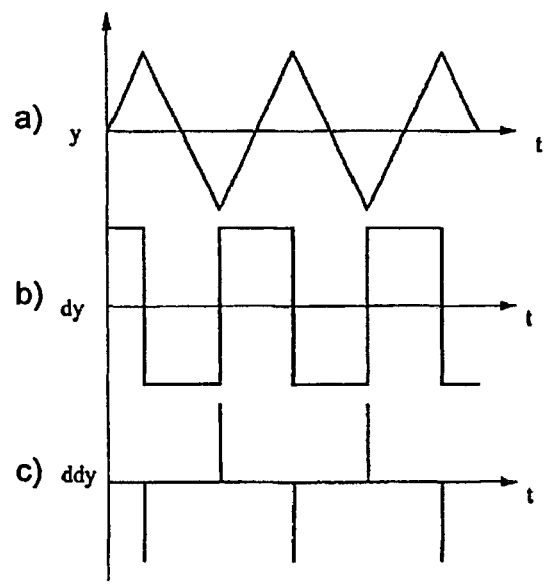

FIG. 2a shows an ideal, noise free output signal b from a process oscillating due to static friction. The oscillating process is integrating. The signal shown in FIG. 2a is triangular and shows the abrupt inclination changes typical for oscillations due to static friction. The abrupt inclination changes of the fundamental form of the output signal will, in a second derivative ddy, form a periodic pulse-train of peaks with alternating signs. FIG. 2b shows the first derivative dy of the output signal in FIG. 2a, and FIG. 2c shows the second derivative ddy of the output signal.

Figures 3A, 3B, 3C:
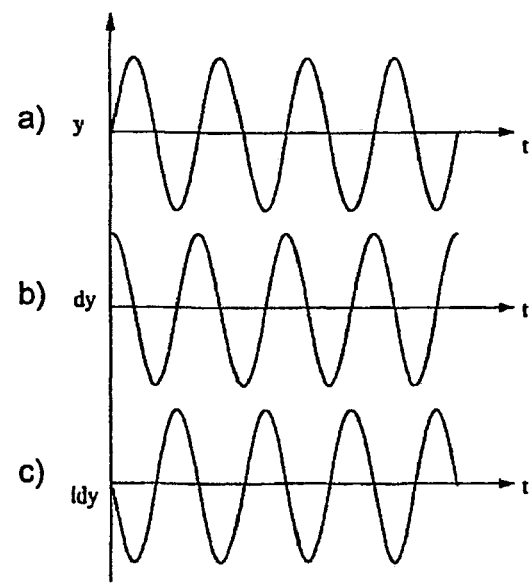

FIG. 3 shows an ideal, noise free output signal y from a process oscillating for another reason. FIGS. 3b and 3c show the first derivative dy and the second derivative ddy of the output signal y. As shown in FIG. 3c, the second derivative of the output signal is a sinus-curve.

By producing information about the second derivative of the output signal from the control process in the form of a probability distribution, the measured signal can be compared with two corresponding probability distributions, the first one representing the output signal at static friction, and the second representing the output signal when there is no static friction. Thus, it is possible to make conclusions about the appearance of static friction. To make it possible to compare the two probability distributions with the probability distribution of the second derivative of the output signal from the control process, it must be represented as a suitable distribution function. Such a probability distribution may, for example, be a sampled histogram.

A sampled histogram can be obtained by dividing the measurements, such as the amplitude, of the filtered second derivative of the output signal into classes. The number of measurements or occurrences of amplitudes in each class are summarized. These may be presented graphically as rectangles whose areas are proportional to the number of measurements in each class. Thereby, the probability for a sample comprising a measurement value $N_i$ of a certain class is calculated by dividing the number of measurements $N_i$ in this class with both the total number of measurements N and the width of the class $\Delta x$. For simplifying the adaption to the probability distribution, the mean value is deleted from the measured data. The measured data will then be oscillating around origin.

To be able to compare the sampled histogram with the first and the second probability distribution, one has to first calculate the ideal expected probability distributions for the first and the second case. For the first case, with static friction, the ideal distribution function can be described as a gaussian distribution with addition of white noise. The gaussian probability distributions $f_{E(x)}$ can be described by the equation $$f_E(x) = \frac{1}{\sqrt{2\pi}\,\sigma} \exp - \frac{(x-\mu^2)}{2\sigma^2}.$$

The gaussian distribution has a maximum. To be able to compare the measured histogram with the second probability distribution, one has to adapt the probability function to the histogram. Such an adaption can easily be achieved by assigning zero to the mean value $\mu$ and varying the standard variation $\sigma$ in the above equation. For achieving as good an adaption as possible, one is searching for the standard deviation giving the best adaption of the gaussian curve to the diagram. This search may, for example, be performed by using the least square method.

Preferably, the standard deviation $\sigma$ calculated from measured data can be used as a start value for iterating a suitable value on the standard deviation $\sigma$.

For further improving the adaption, the gaussian graph may have a further contribution such as a uniform distribution within an interval corresponding to the maximum measured amplitude for the output signal from the process. The probability distribution is obtained by doing a weighed summarizing of the gaussian graph and the uniform distribution.

For the second case, wherein the signal is ocsillating for any other reason than static friction, the ideal distribution graph is based on a sinus signal with addition of white noise. This probability distribution may for example be described by the following equation:

$$f_z(z) = \frac{1}{\sigma\sqrt{2\pi^3}} \int_{-A}^{A} \frac{\exp\left(-\frac{(z-x-\mu)^2}{2\sigma^2}\right)}{\sqrt{A^2 - x^2}}\,dx.$$

If the standard deviation $\sigma$ is essentially less than A, this probability distribution has two maxima and thus differs essentially form the gaussian graph. Due to the fact that the graph has two maxima, it is called the Camel graph in the following. This integral has no analytic solution and therefore it must be calculated numerically. Three parameters in the equation must be decided if a solution shall be obtained. Those parameters are the mean value $\mu$, which is assigned to the value zero, since used data have a mean value of zero, the oscillating amplitude A for the measured signal, which is calculated by any known algorithm, and the standard deviation a which is calculated for adapting of the distribution graph to the sampled histogram. This adaption can be obtained by a standard algorithm using a least square adaption.

It is important to set up a limit for the standard deviation $\sigma$ to prevent the probability distribution from converting into a gaussian distribution, i.e. both maxima will merge into one. This could happen if the estimated value for the standard deviation a is too large in relation to the oscillating amplitude A. To avoid this to happen at the adaption, may for example the permitted values of the standard deviation $\sigma$ be limited so that it becomes significantly smaller than the oscillating amplitude A at the least square adaption. Preferably, the condition $\sigma < 0.4$ A shall be applied.

Figures 4A, 4B, 4C, 4D:
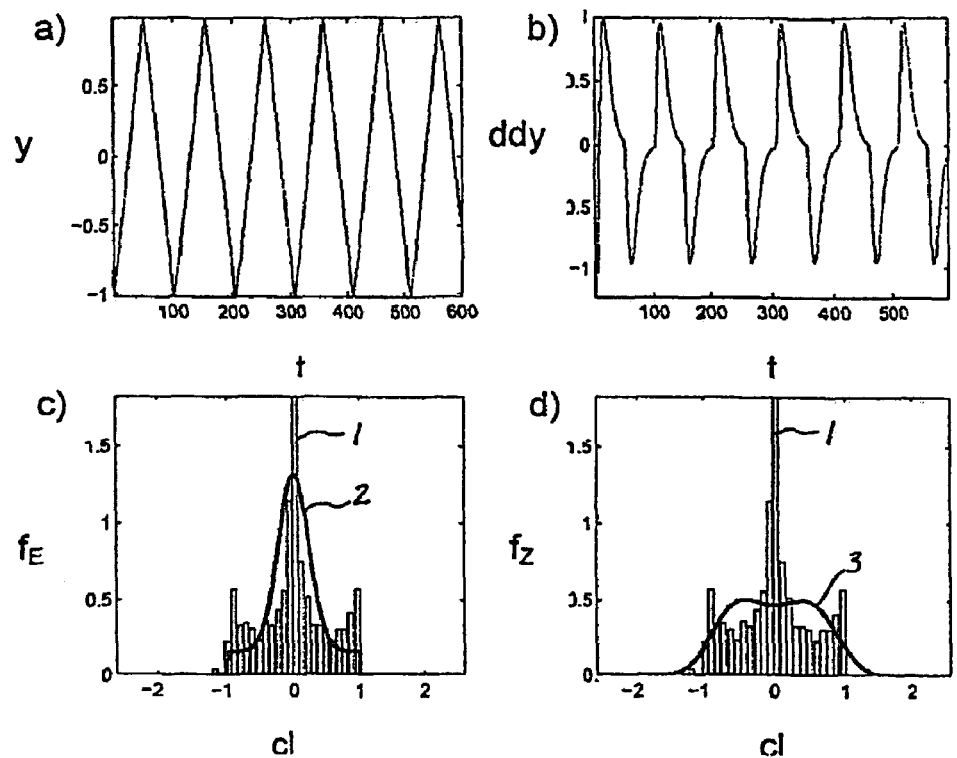
FIGS. 4a, 4b show the measured output signal and its filtered second derivative for a control process with static friction.
FIGS. 4c, 4d show the probability distribution for the derived signal in FIG. 4b as a histogram and a first and a second theoretically calculated probability distribution that have been adapted to the histogram.

The FIGS. 4a–4d show the method applied on ideal values from an integrating control system oscillating due to static friction. FIG. 4a shows the ideal output signal y, and FIG. 4b shows its second derivative ddy. FIG. 4c and FIG. 4d show the probability distribution as a histogram 1 based on the second derivative ddy. In FIG. 4c a first probability distribution 2 is shown as a gaussian graph, which has been adapted to the histogram 1. In FIG. 4d, a second probability distribution 3 is shown as a Camel graph, which has been adapted to the histogram 1. It is clear from the figures that the gaussian graph fits better to the histogram than the Camel graph.

Figures 5A, 5B, 5C, 5D:
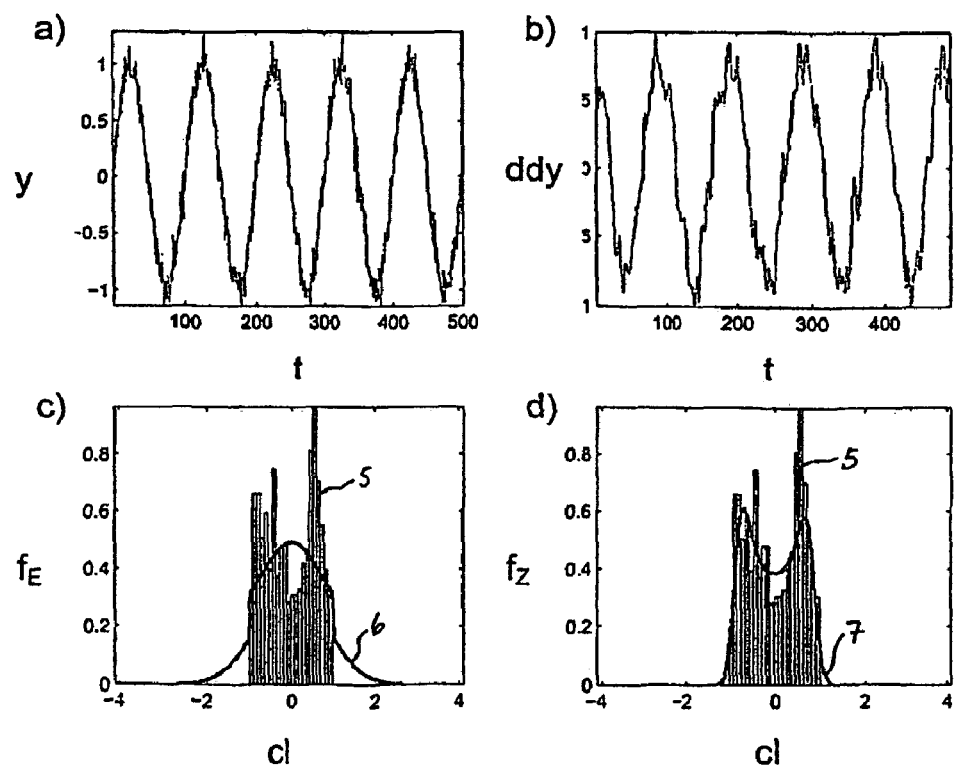
FIGS. 5a, 5b show the measured output signal and its filtered second derivative for a control process oscillating for another reason than static friction.
FIGS. 5c, 5d show the probability distribution for the derived signal in FIG. 5b as a histogram and a first and a second theoretically calculated probability distribution that have been adapted to the histogram.

The FIGS. 5a–5d show the method applied to ideal values from an integrating control system oscillating for any other reason than static friction. FIG. 5a shows the output signal y, and FIG. 5b shows its filtered second derivative ddy. The FIGS. 5c and 5d show the probability distribution for the second derivative ddy as a histogram 5. In FIG. 5c, a first probability distribution 6 is shown as a gaussian graph, which has been adapted to the histogram 5. In FIG. 5d, a second probability distribution 7 is shown as a Camel graph, which has been adapted to the histogram 5. It appears from the figures that the Camel graph with its two maxima fits better to the histogram than the gaussian graph.

When the measured, filtered, and derived signal has been mapped in a probability distribution, such as a sampled histogram, it is compared with the ideal probability distributions, representing the two oscillating cases due to static friction and another reason. If the fitting is significantly better with the first probability distribution than with the second, the conclusion is that the oscillations are caused by current static friction. In the opposite case, the conclusion is that the oscillations are caused by something else. If the fitting with both the ideal probability distributions is approximately the same, no conclusion is made. The comparison may advantageously be automatic by calculation of a first value, corresponding to the difference between the first and the second probability distribution, and a second value corresponding to the difference between the first and the third probability distribution. It is advantageous to use the mean square error (MSE) for estimating the fitting between the probability distributions. Thereafter, the comparison of the first and the second value can be made by a conclusion condition, for example, if the values differ more than 10% and the first value is less than the second value, there is static friction.

Alternative inventive embodiments for separating oscillating signals comprising abrupt inclination changes from others that do not are, for example, Fourier Analysis, mathematical modeling, or another signal processing. A method comprising Fourier Analysis may for example involve studying the frequency spectrum of the signal and detecting narrow or wide peaks, which may correspond to both said signal shapes, i.e. the triangular wave and the sinus wave illustrated in FIG. 2a and FIG. 3a. In a method comprising mathematical modeling, the signal is described with a mathematical model. This description may later be used in an algorithm detecting specific properties in the calculated model.

The above-described method according to the invention may also be used for self-regulating processes. For self-regulating processes, the first derivative of the output signal is used, differing from the case with an integrating process, wherein the second derivative of the output signal is used.

It must be realized that a number of variants and alternative embodiments of the inventive method is being within the frame of the invention is obvious for a man skilled in the art. For instance, the number of derivations depends on which control process is intended, and where in the system the signals are measured.

In a further embodiment of the method according to the invention, other mapping functions than said histogram may be used for taking advantage of the statistical information according to the idea of the invention intended, for example a frequency spectrum, visual view of the mappings, or mathematical modeling of the signals, parametric as well as non-parametric.

The calculated probability distributions, which have been adapted to and compared with the probability distribution for the measured values may be formed in different ways. One way is to analytically calculate the theoretic probability distribution for a derived triangular signal with the addition of white noise.

The invention claimed is:

1. A method for evaluation whether oscillations in a control process depend on static friction in an actuator, comprising:
    measuring the signal from the actuator or the signal from the process;
    deriving the measured signal at least once;
    calculating a first mapping of the derived signal;
    calculating a second mapping representing an output signal at static friction;
    calculating a third mapping representing an output signal without static friction;
    comparing the first mapping with the second mapping and the third mapping
    signal processing the measured signal for the purpose of detecting whether the measured signal comprises abrupt inclination changes; and
    deciding based on the derived signal whether there is static friction in the actuator based on whether the signal comprises abrupt inclination changes in dependence of the comparison.

2. The method according to claim 1, wherein the third mapping represents an output signal oscillating essentially sinusoidally.

3. A method for evaluation whether oscillations in a control process depend on static friction in an actuator, comprising:
    measuring the signal from the actuator or the signal from the process;
    calculating a frequency of the measured signal;
    filtering the measured signal with a filter having a filter bandwidth in an interval 2–4 times the calculated frequency;
    signal processing the measured signal for the purpose of detecting whether the measured signal comprises abrupt inclination changes; and
    deciding whether there is static friction in the actuator based on whether the signal comprises abrupt inclination changes.

4. A method for evaluation whether oscillations in a control process depend on static friction in an actuator, comprising:
    measuring the signal from the actuator or the signal from the process;
    deriving the measured signal at least once;
    calculating a first probability distribution for the derived measured signal;
    calculating a second probability distribution representing an output signal at static friction;
    calculating a third probability distribution representing an output signal oscillating for a reason other than static friction;
    comparing the first probability distribution with the second probability distribution and the third probability distribution;
    signal processing the measured signal for the purpose of detecting whether the measured signal comprises abrupt inclination changes; and
    deciding based on the comparison of the probability distributions whether there is static friction in the actuator based on whether the signal comprises abrupt inclination changes.

5. The method according to claim 4, wherein the second probability distribution has a maximum and in that the third probability distribution has two maxima.

6. The method according to claim 4, wherein, before the comparison, an adaption of the second and the third probability distribution to the calculated probability distribution of the derived signal is performed.

7. The method according to claim 6, wherein said adaption is performed by estimating, for each of the second and third probability distribution, the standard deviation rendering the best adaption to the probability distribution for the derived signal.

8. The method according to claim 7, wherein the amplitude for the oscillations in the measured signal is estimated and the standard deviation for the third probability distribution shall be less than 40% of the amplitude.

9. The method according to claim 4, wherein the second probability distribution represents an output signal mainly comprising white noise and the probability distribution has an essentially gaussian shape.

10. The method according to claim 4, wherein the third probability distribution represents an output signal comprising a sinusoidal signal and white noise.

11. The method according to claim 4, wherein said comparison is performed by calculating a first value corresponding to the difference between the first and the second probability distribution, and a second value corresponding to the difference between the first and the third probability distribution, and comparing the first and the second value with each other, and if the values differ with more than 10% and the first value is less than the second value, there is static friction.

12. A system for evaluation whether oscillations in a control process depend on static friction in an actuator, comprising:
    a measuring device for measuring the signal from the actuator or the signal from the process;
    a signal processing means that decides whether the measured signal comprises abrupt inclination changes;
    a derivation means for determining the first and the second derivative of the measured signal;
    a calculation member which, based on the derivative of the measured signal, calculates one or several values which depend on whether there is static friction in the actuator, wherein the calculation member is adapted for calculating a first mapping of the derived signal and for comparing the first mapping with a second mapping representing an output signal at static friction, and a third mapping representing an output signal without static friction and calculating the values based on the comparison.

13. The system according to claim 12, wherein the mappings comprise probability distributions and wherein the third mapping represents an output signal oscillating essentially sinusoidally.

14. A system for evaluation whether oscillations in a control process depend on static friction in an actuator, comprising:
    a measuring device for measuring the signal from the actuator or the signal from the process;
    a signal processing means that decides whether the measured signal comprises abrupt inclination changes; and
    a filter operative to filter the measured signal, wherein the filter has a filter bandwidth in the interval 2–4 times the frequency of the measured signal.

15. A computer program product loadable into the internal memory of a computer, comprising:
    software code portions for performing the following steps when they are run on a computer:
    receiving measuring data from a control process comprising an actuator, which measuring data either correspond to measured values of the signals from the actuator or measured values for the signal from the process
    deriving the measured signal at least once,
    signal processing the measured signal for the purpose of determining whether the measured signal comprises abrupt inclination changes,
    calculating a first mapping of the derived measured signal,
    calculating a second mapping representing an output signal at static friction,
    calculating a third mapping representing an output signal without static friction,
    comparing the first mapping with the second mapping, and the third mapping, and
    calculating based upon the comparison at least one at least one valued depending upon whether there is static friction in the actuator based upon the derivative of the measured signal.

16. The computer program product according to claim 15, wherein the first mapping and the second mapping comprise probability distributions and the third mapping represents an output signal oscillating essentially sinusoidally.

* * * * *